(12) United States Patent
Chanduszko

(10) Patent No.: US 10,368,991 B2
(45) Date of Patent: Aug. 6, 2019

(54) DEVICE AND ASSOCIATED PERCUTANEOUS MINIMALLY INVASIVE METHOD FOR CREATING A VENOUS VALVE

(71) Applicant: C.R. Bard, Inc, Tempe, AZ (US)

(72) Inventor: Andrzej J. Chanduszko, Chandler, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 15/425,353

(22) Filed: Feb. 6, 2017

(65) Prior Publication Data

US 2018/0221151 A1    Aug. 9, 2018

(51) Int. Cl.
| | |
|---|---|
| A61F 2/24 | (2006.01) |
| A61F 2/90 | (2013.01) |
| A61F 2/915 | (2013.01) |
| A61F 2/95 | (2013.01) |

(52) U.S. Cl.
CPC .............. *A61F 2/2475* (2013.01); *A61F 2/90* (2013.01); *A61F 2/915* (2013.01); *A61F 2/95* (2013.01); *A61F 2002/91575* (2013.01); *A61F 2002/91583* (2013.01); *A61F 2230/0008* (2013.01); *A61F 2230/0017* (2013.01); *A61F 2230/0054* (2013.01); *A61F 2230/0056* (2013.01); *A61F 2230/0069* (2013.01); *A61F 2230/0091* (2013.01)

(58) Field of Classification Search
CPC ..... A61F 2/2418; A61F 2/2412; A61F 2/2475
USPC ................................ 623/1.15–1.24
See application file for complete search history.

(56) References Cited

U.S. PATENT DOCUMENTS

| | | | |
|---|---|---|---|
| 2003/0153875 A1* | 8/2003 | Ostfeld ............. | A61M 25/0017 604/171 |
| 2004/0249408 A1* | 12/2004 | Murphy ................ | A61F 2/2487 606/198 |
| 2005/0085775 A1* | 4/2005 | Ostfeld ............. | A61M 25/0017 604/171 |
| 2006/0184237 A1* | 8/2006 | Weber ....................... | A61F 2/07 623/1.44 |
| 2009/0043288 A1* | 2/2009 | Petrakis .............. | A61M 31/002 604/890.1 |
| 2011/0245851 A1* | 10/2011 | Ducharme ......... | A61B 17/0057 606/151 |
| 2011/0293667 A1* | 12/2011 | Baksh ................. | A61L 27/3804 424/400 |
| 2013/0197622 A1* | 8/2013 | Mitra .................... | A61L 31/145 623/1.15 |
| 2013/0211489 A1* | 8/2013 | Makower ................ | A61F 2/915 623/1.2 |
| 2013/0218258 A1* | 8/2013 | Ko ........................... | A61F 2/06 623/1.15 |

(Continued)

FOREIGN PATENT DOCUMENTS

WO    WO 2009052207 A2 *  4/2009  ........... A61F 2/2412

*Primary Examiner* — Suzette J Gherbi
(74) *Attorney, Agent, or Firm* — Rutan & Tucker, LLP

(57) ABSTRACT

A device includes a stent scaffold structure supporting a patch on an interior surface thereof. The device may be used to produce a neovalve in a percutaneous minimally invasive manner. Exemplary methods include implanting the device, permitting a growth layer to form over at least a portion of the patch, and separating the patch from the stent scaffold thereby forming a slit or gap in the vessel wall to act as a valve similar to the surgical neovalve.

12 Claims, 10 Drawing Sheets

(56) References Cited

U.S. PATENT DOCUMENTS

| | | | |
|---|---|---|---|
| 2014/0036263 A1* | 2/2014 | Kim | G01N 21/658 356/301 |
| 2016/0120706 A1* | 5/2016 | Collinson | A61F 13/0253 604/319 |
| 2017/0128072 A1* | 5/2017 | Wang | A61B 34/73 |
| 2018/0164221 A1* | 6/2018 | Singh | A61K 45/06 |

* cited by examiner

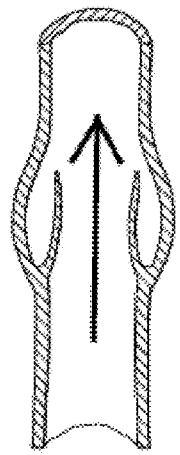 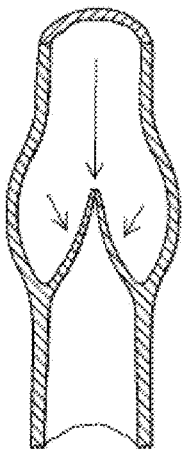 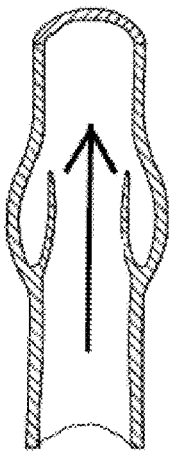 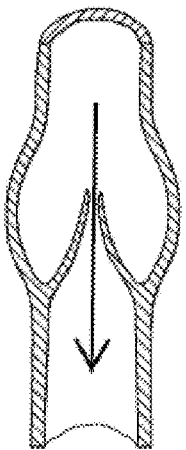
FIG. 1A   FIG. 1B   FIG. 1C   FIG. 1D
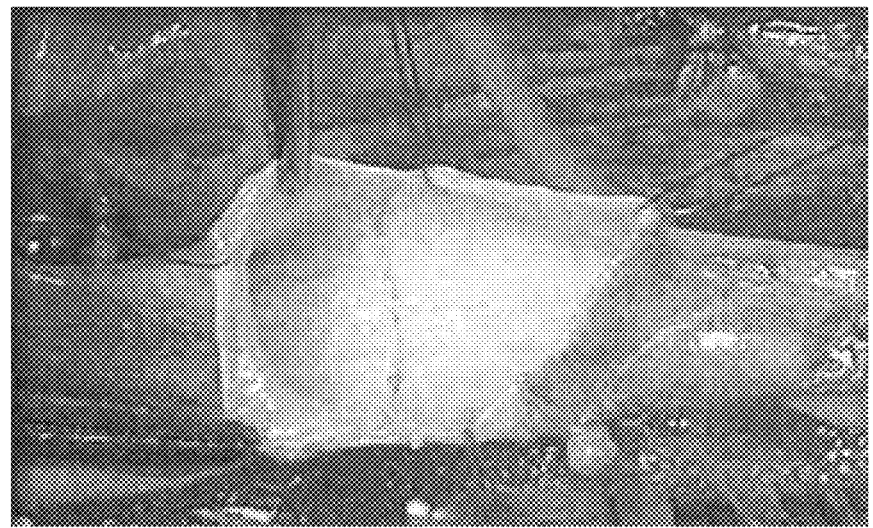
FIG. 2A

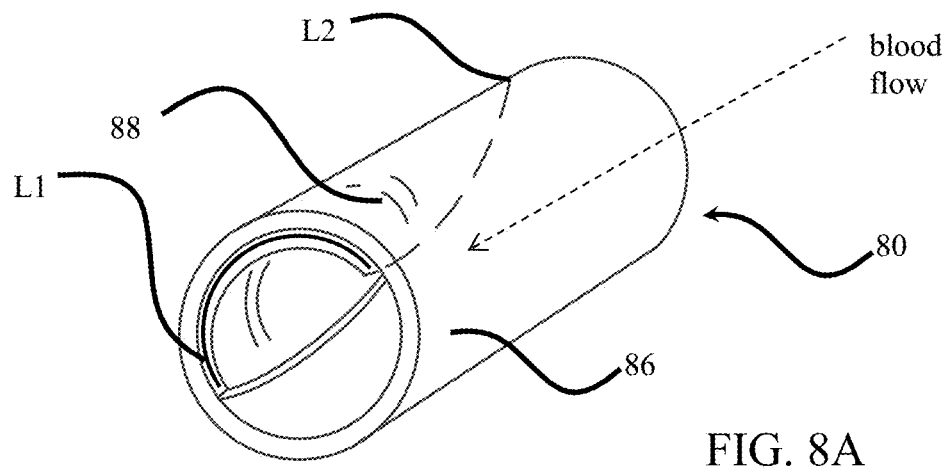
FIG. 8A
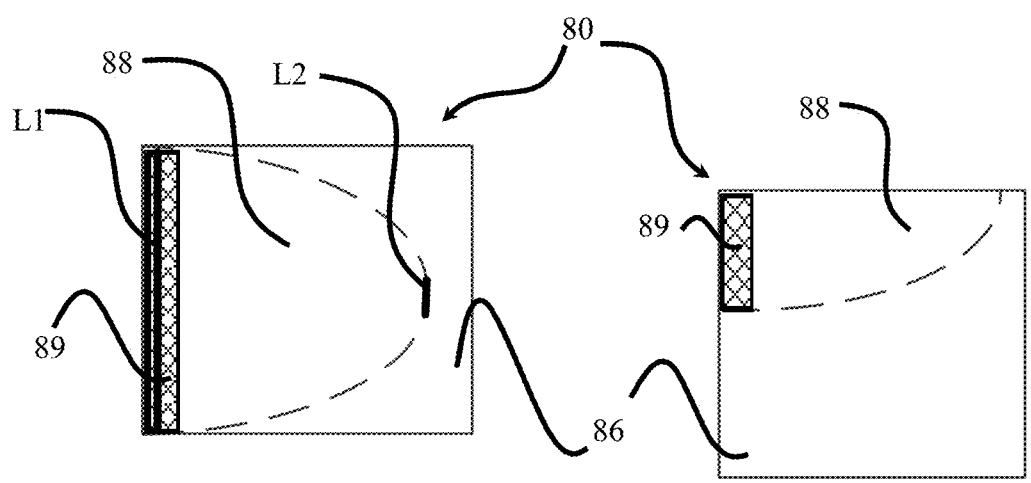
FIG. 8B
FIG. 8C

DEVICE AND ASSOCIATED PERCUTANEOUS MINIMALLY INVASIVE METHOD FOR CREATING A VENOUS VALVE

BACKGROUND

Chronic venous insufficiency (CVI) is a long-term condition caused by malfunctioning (incompetent) valves in the veins. It may also occur as the result of a past blood clot in the legs. CVI is a medical condition where the valves of the vein do not fully close and permit blood to travel upstream. The condition causes blood to pool in the legs. FIGS. 1A-1B illustrate an exemplary vein having a properly functioning valve in which blood may pass through the vein in a single direction back to the heart. FIGS. 1C-1D illustrate an exemplary vein suffering from chronic venous insufficiency in which the vein valve does not fully close and thereby permits blood to flow away from the heart. Typical symptoms include swelling of the legs, varicose veins and ulcers.

Currently, the only effective way to replace a damaged valve is surgery to either modify an existing valve or create a new valve by separating venous wall layers. However, these methods are extremely invasive and require the external access to the vein through dissection. FIGS. 2A-2C illustrate an exemplary deep venous reconstruction surgery in which the vein is opened in FIG. 2A, the venous layers are dissected in FIG. 2B, and a valve is created from the dissected layers in FIG. 2C. As illustrated, the surgery is very invasive requiring external vein dissection, reconstruction, and closure.

SUMMARY

Exemplary embodiments include a device that can be used to produce a neovalve. Exemplary embodiments include a stent, stent-like scaffold, or other support structure (generally referred to as stent herein) to position or retain a patch along a portion of a vessel wall. The exemplary embodiment may also include a patch removably attached to the stent. The patch may be on a luminal surface of the stent and may traverse only a portion of the interior circumference of the stent, such that the patch does not fully encircle the lumen of the stent. A portion of the patch may be coated or otherwise have a layer, surface structure, or other feature to inhibit or enhance endothelial, smooth muscle cell, or other tissue layer (hereinafter referred to as growth layer) proliferation.

Exemplary embodiments include a method to produce a neovalve in a percutaneous minimally invasive manner using exemplary embodiments of the device described herein. In an exemplary embodiment, a device comprising a stent and a patch removably attached to an interior surface of a stent is provided. The device may be delivered percutaneously and minimally-invasively to a desired location to form a replacement vein valve. The device may be delivered, deployed, and left in place at the target vein for sufficient time to form a growth layer on at least a portion of the patch. For example, the device may be implanted for approximately 4-8 weeks or other period of time determined to be suitable. After the patch is covered by the growth layer, such as completely covered, or substantially covered, the patch is separated from the stent and removed from the body. In an exemplary embodiment, the patch is substantially covered while a retrieval device remains uncovered and positioned near a center of the vessel. In this case, the patch is separated and removed by engaging the retrieval device and imposing an external force on the patch, thereby separating it from the stent. In an exemplary embodiment, the retrieval device is engaged by a snare. In an exemplary embodiment, the retrieval device comprises an extension that reaches to an exterior position outside of the body, when the patch is positioned within the body and covered by the growth layer. An external force is applied to the extension, which translates through the body to the patch, and thereby separating the patch from the stent.

Exemplary embodiments include creating a slit or flap at a vessel wall by separating the growth layer from a vessel wall lumen and/or from a stent. In order to aid in the removal of the patch, and/or in the creation of the slit in the vessel wall, the method may include inhibiting the proliferation of cells at a portion of the patch. Therefore, the patch may be coated or otherwise have a layer, surface structure, or other feature to inhibit cell proliferation. An exemplary embodiment may therefore include exposing a leading edge of the patch by inhibiting an vascular tissue layer from forming thereover during the implanted duration. Exemplary embodiments use the space left behind after the patch is removed from within the vessel wall to cause the vessel wall layers to be separated due to the blood flow. Exemplary embodiments therefore may permit the luminal side of a vessel wall to act as a valve similar to the surgical neovalve.

DRAWINGS

FIGS. 1A-1D illustrate and exemplary human vein in cross section having a valve either properly function in an open and closed configuration or improperly functioning in an open and incompletely closed configuration.

FIGS. 2A-2C illustrate photographs taken from an invasive conventional surgical procedure to replace a damaged valve. See Maleti, O., Deep Venous Reconstructive Surgery for C.V.I. New Procedures and Tricks. Controversies and Updates in Vascular Surgery, January 2014.

FIG. 8A-8C illustrate exemplary devices for creating a neovalve according to embodiments.

DESCRIPTION

Figure 2B:
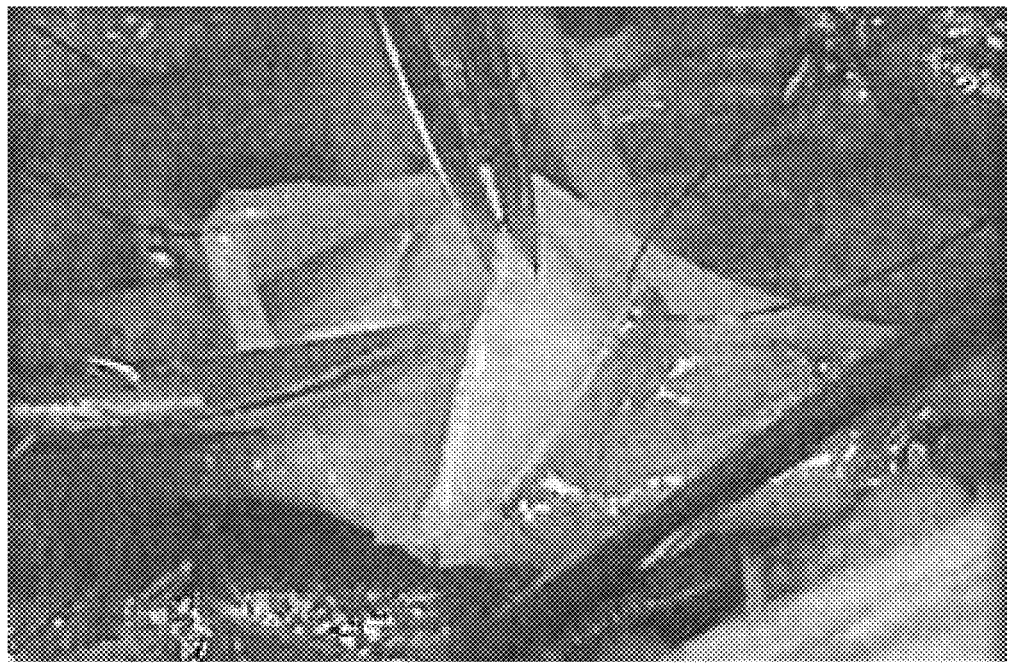
Figure 2C:

The following detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. It should be understood that the drawings are diagrammatic and schematic representations of exemplary embodiments of the invention, and are not limiting of the present invention nor are they necessarily drawn to scale.

Exemplary embodiments described herein include a device to produce a neovalve through a percutaneous minimally-invasive method. Exemplary embodiments include a stent or stent-like scaffold and patch removeably attached to the scaffold. The device may include a retrieval component to remove the patch from the scaffold. Methods of creating the neovalve may include delivering the device to the target vein and leaving the device in place according to known stenting methods. After a sufficient period of time, such that the device is covered by a growth layer, the patch may be removed which creates a slit in the vessel wall. The space left behind the patch within the vessel wall may be used to cause the vessel wall layers to separate and permit the luminal side of the wall to act as a valve similar to the surgical neovalve.

Although embodiments of the invention may be described and illustrated herein in terms of a stent support structure, it should be understood that embodiments of this invention are not so limited, but are additionally applicable to other support structures in which a patch is held against a luminal vessel wall. Furthermore, although embodiments of the invention may be described and illustrated herein in terms of exemplary retrieval components, it should be understood that embodiments of the invention can use any combination of retrieval method or mechanism.

Stent constructions generally include cylindrical frames that are expandable from a collapsed, reduced diameter delivery configuration to a deployed, larger diameter configuration for support and/or contact of the luminal vessel wall. In an exemplary embodiment, the stent frame defines a plurality of openings that facilitate tissue ingrowth.

There are two broad classes of stents: self-expanding stents and balloon expandable stents. Self-expanding stents are typically characterized by intraluminal expansion when a constraining force is removed, such as an outer sheath of a stent delivery system, and/or in the presence of an elevated temperature (due to material properties of the stent). Self-expanding stents are generally loaded into a stent delivery system by collapsing the stent from an expanded configuration at a first larger diameter to a collapsed configuration at a second smaller diameter. Balloon expandable stents are typically characterized by intraluminal expansion via an inflation force, such as a balloon catheter. Balloon expandable stents are generally loaded onto a balloon catheter through a crimping process to transition the stent to a collapsed configuration, and are plastically deformed when the balloon is inflated in the body vessel to the expanded configuration.

There are two basic architectures for stents, circumferential and helical. Circumferential configurations generally include a series of cylindrical rings, formed by a series of connected struts, joined together by connecting elements or bridges along a longitudinal axis of the stent. Helical configurations include a continuous helical structure along the longitudinal axis of the stent with adjacent windings, formed by a series of connected struts, connected by one or more connecting elements or bridges.

Any scaffold structure may be used to support the patch described herein. For example stents described in U.S. Pat. Nos. 6,488,703; 6,579,314; 8,518,101; 9,066,825; 9,265,636; and 9,561,123 may be used. The disclosure of each is hereby incorporated by reference in its entirety herein.

The patterns shown and described herein may be incorporated into any intraluminal prosthesis, such as a self-expanding stent or a balloon expandable stent, and helical or circumferential configurations, without limitation. In one embodiment, the patterns disclosed herein may be machined (e.g., laser machined) into a seamless tube of metal or polymer. Non-limiting examples of potential metal tubes include stainless steel (e.g., AISI 316 SS), titanium, cobalt-chromium alloys, and nickel titanium (Nitinol). In other embodiments, the patterns disclosed herein may be formed into a sheet of metal or polymer that is rolled into a tubular shape. The tubes or sheets may be heat-treated prior to machining the pattern therein, and the machined tubes or sheets may be annealed and/or electro-polished. Other known pre-processing and post-processing methods are also contemplated herein. The pattern of struts and connecting elements can be configured depending on the desired attributes. For example, the pattern can be configured to enhance flexibility or bendability. The pattern can also be configured to ensure uniform expansion and prevent foreshortening of the stent upon intraluminal expansion. The pattern can also be configured to facilitate tissue growth over the structure and attached patch.

Figure 3:
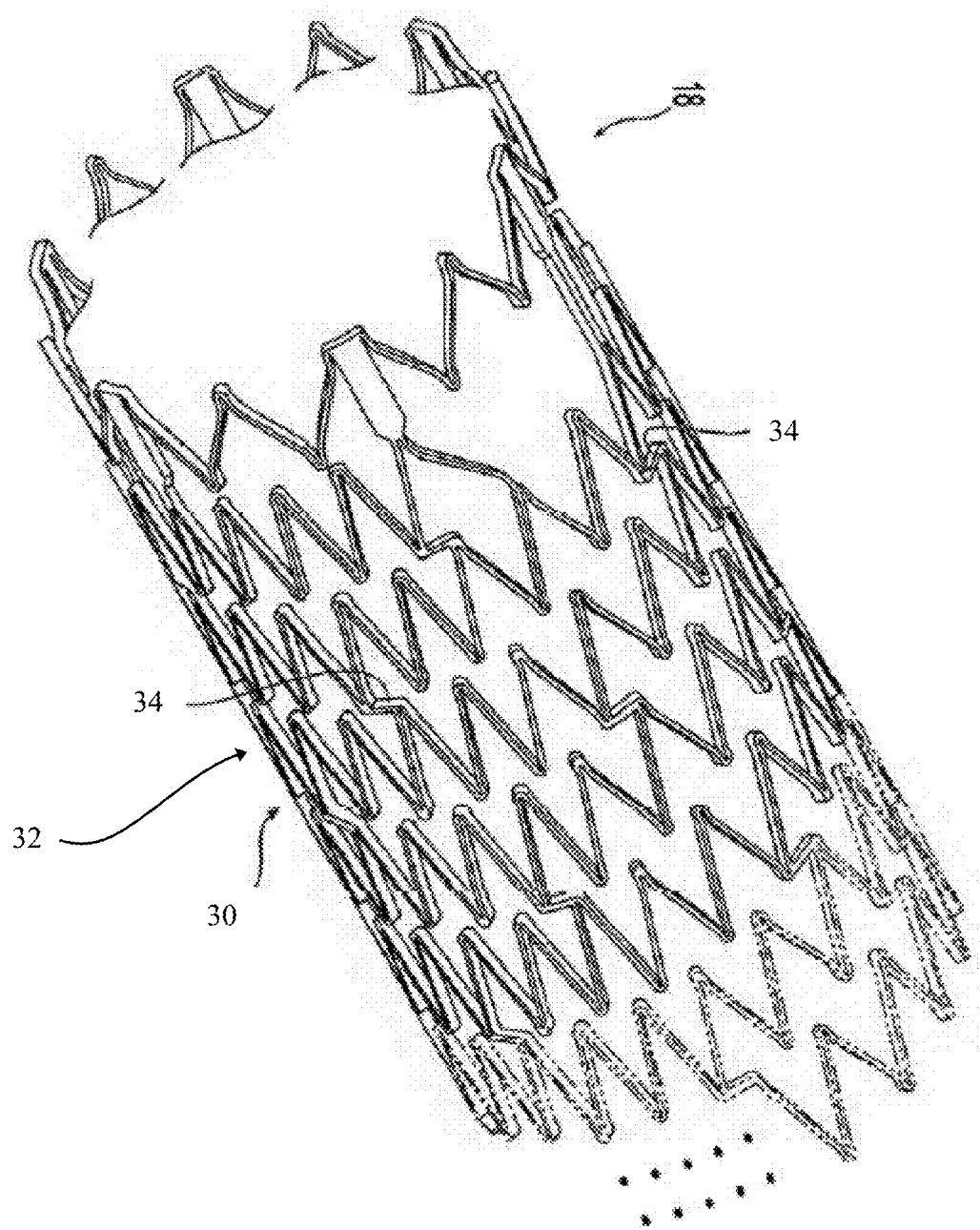
FIGS. 3-7 illustrate exemplary representative stents and stent scaffolding structures the may be used in exemplary embodiments.

FIG. 3 illustrates an exemplary stent structure comprising a helical stent construction. In an exemplary embodiment, the stent 30 has a tubular shape and a first end, a second end, an intermediate portion, and a longitudinal axis. The intermediate portion includes a continuous helical winding 32. The winding 32 has a plurality of circumferential sections that join together end-to-end and circumscribe the axis from the first end to the second end, with the continuation of each circumferential section along the path of the helical winding represented with dashed lines in FIG. 3. The portions of the stent in the background of the figure are not shown in detail, for clarity and to clearly show identical features already presented in the foreground of the figure. Although only one helical winding is illustrated in FIG. 3, more than one helical winding can be employed in the stent. For example, a helical winding with a first helical angle can be connected or coupled with another helical winding that has a different second helical angle. Alternatively, the helical winding can be used as a central portion of the intermediate portion and a different helical winding can be used proximate each end of the intermediate portion. As shown, the stent may include at least one bridge 34 configured to connect one circumferential section to an axially-spaced adjacent circumferential section. The bridge may extend generally circumferentially around the axis 16 on a generally orthogonal plane with respect to the axis, or may extend generally parallel with the axis or along any angle in between. Preferably, a plurality of bridges 34 interconnect circumferential sections to adjacent circumferential sections.

Figure 4:
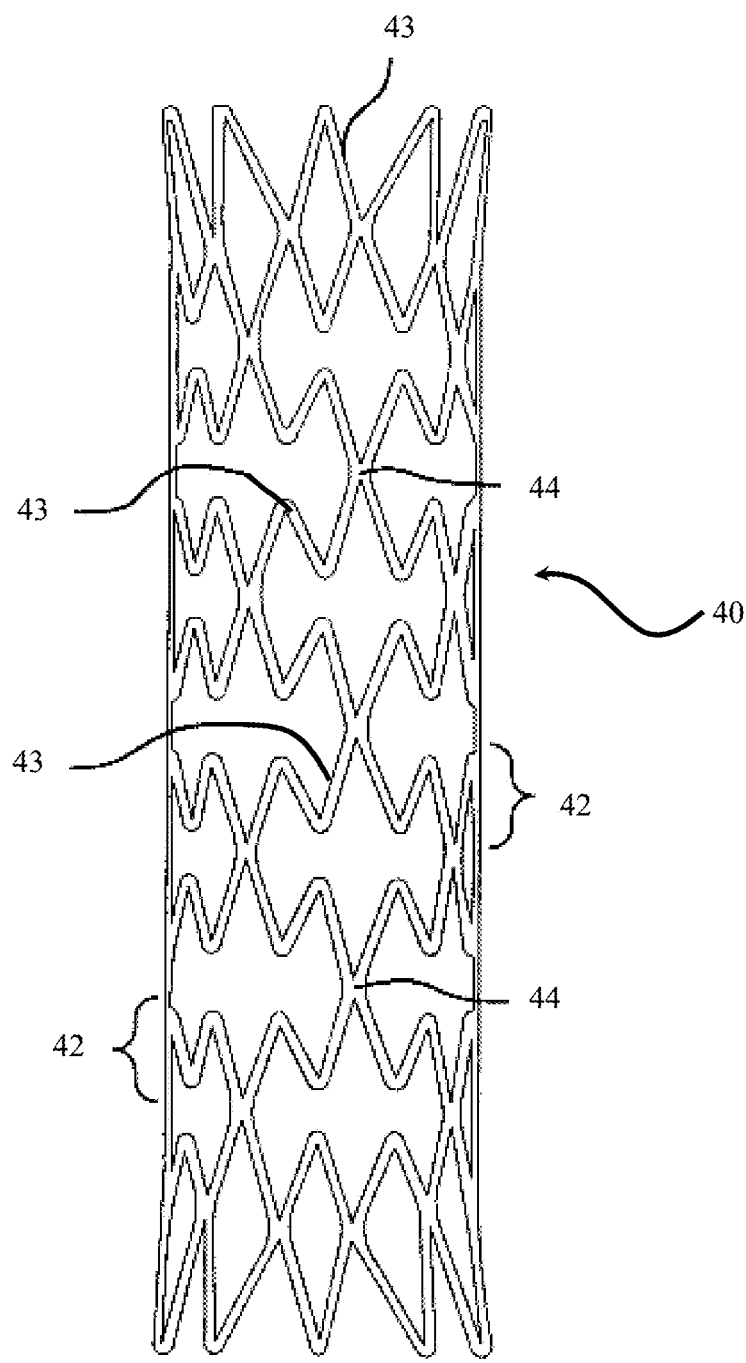
Figure 5:
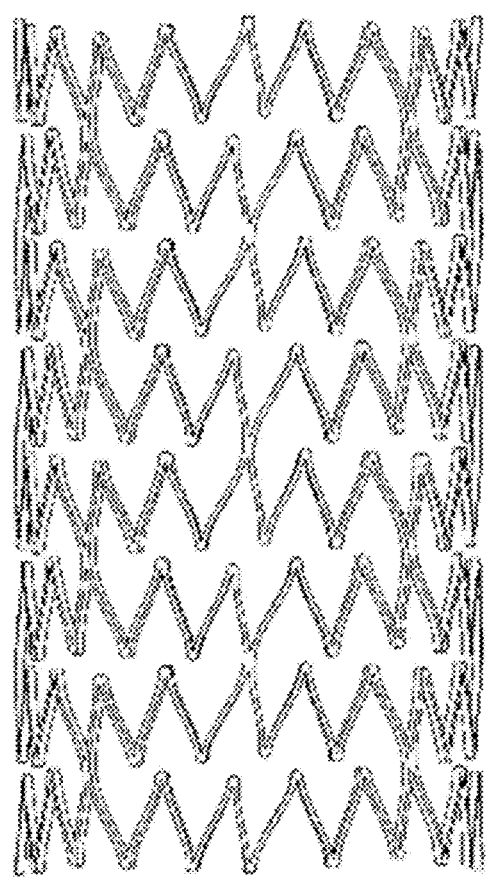

FIGS. 4-5 illustrate exemplary circumferential stent configurations. As shown, the stent 40 defines a single unitary piece that conceptually comprises a plurality of rings stents 42 joined by bridges 44. The ring stents 42 may comprise a plurality of zig-zag struts 43 of the same or different lengths. FIG. 4 illustrates an exemplary stent construction having struts of approximately the same length, while FIG. 5 illustrates an exemplary stent construction having struts of different lengths to offset facing apex of joined struts from adjacent stent rings. The bridges, similar to the disclosed helical configuration may be parallel, orthogonal, or any angular orientation in between with respect to the stent axis.

Figure 6:
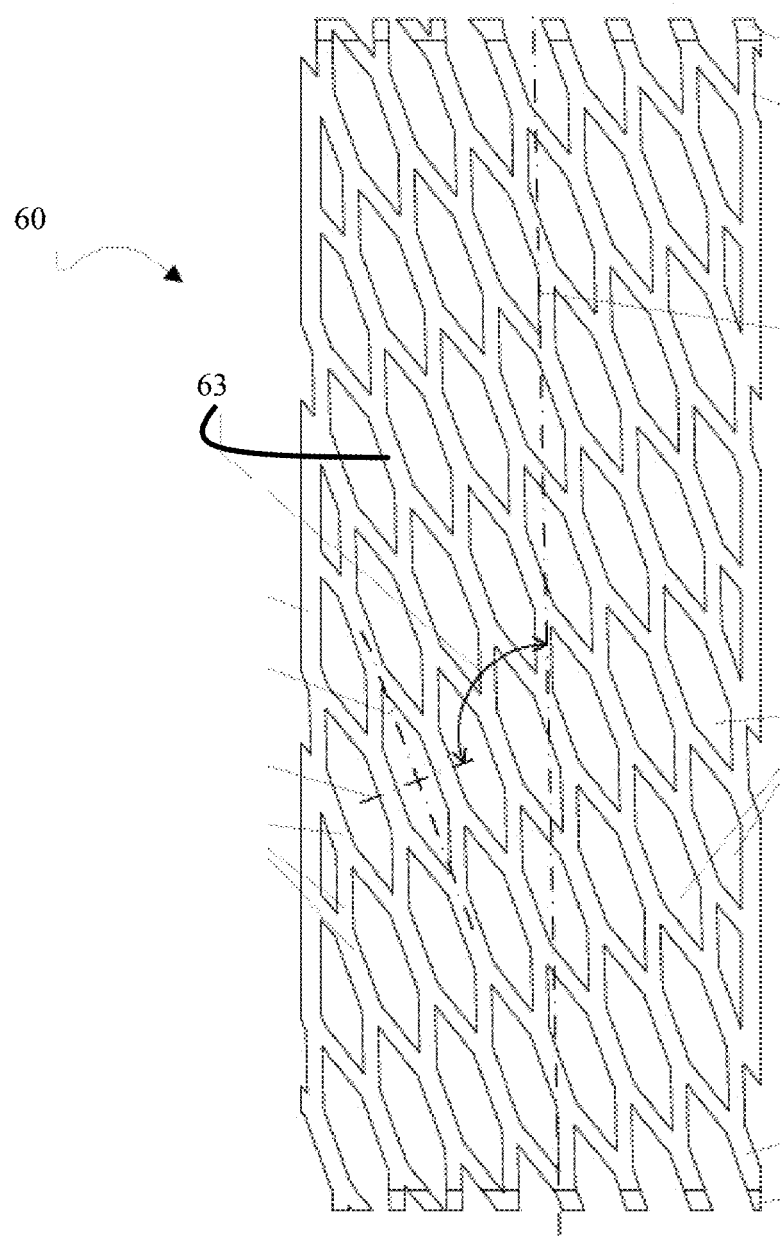

FIG. 6 illustrates an exemplary stent configuration integrating concepts of the helical and circumferential structures into a single construction. As shown, the stent 60 comprises a stent body that can be hollow and generally cylindrical. The stent body can include a plurality of struts 63. Further, the struts can establish a plurality of cells within the stent body. The struts can be in the form of an interconnected network or matrix that is generally continuous. The struts can form a repeating pattern that can define an array of cells. The cells, as shown, can be closed. However, it is noted that the stent may have localized areas in which other struts do not form closed cells. In other words, the stent can be a closed-cell stent in which each cell is separate from adjacent cells. Alternatively, the stent can be an open-cell stent in which one or more struts between two or more adjacent cells is removed from the construction of the stent. In a particular embodiment, as shown, each cell can be hexagonally shaped. Alternatively, each cell can be generally diamond shaped, generally elliptical, or another shape that can allow the stent to be collapsed as described herein. A string or plurality of cells can be aligned helically or arranged circumferentially around the stent body.

Figure 7:
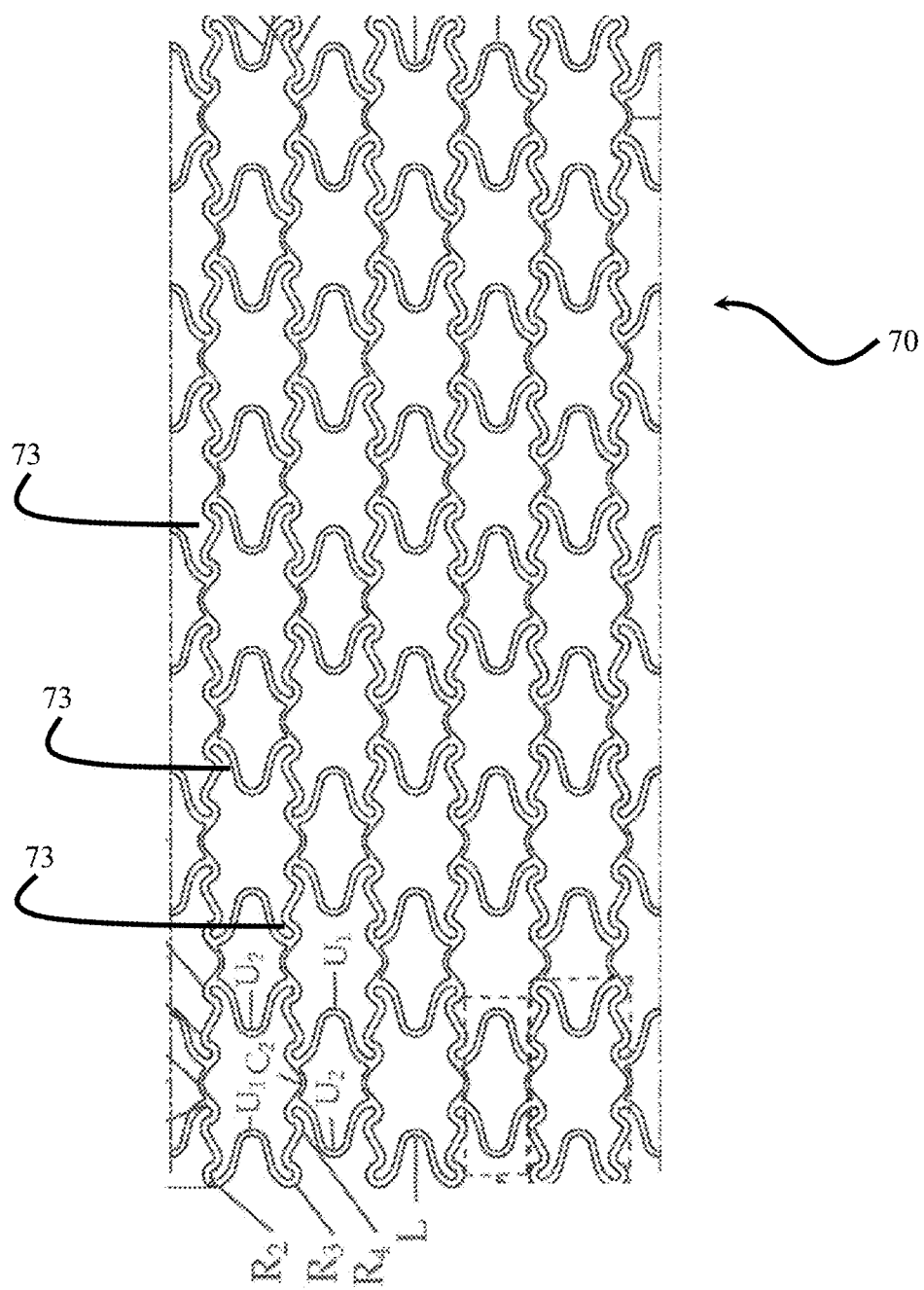

FIGS. 3-6 illustrate stent constructions comprising generally straight struts when in a contracted or delivery configuration. However, stent struts can have any configuration. For example, as shown in FIG. 7, the strut pattern may be generally curved or a combination of straight and curved. Referring to FIG. 7, a stent 70 is shown, including a sequentially repeating pattern of stent cells aligned along a series of circumferential axes perpendicular to a longitudinal axis. Any number of circumferential axes along which the pattern of stent cells is arranged is possible, depending on various stent dimensional features including, for example, overall stent length, stent cell length, connector length, etc. The stent cells are formed by stent struts 73 described herein according to how these cells resemble various letters, the stent elements repeating along the circumferential axes. Beginning from the top left side of FIG. 7, a repeating series of stent struts is shown along a first side of the stent cells, the stent elements including R shapes and U shapes, i.e., R-shaped stent elements and U-shaped stent elements. According to one embodiment, the R-shaped stent elements are similar or identical to those described in U.S. Pat. No. 6,821,292, which is incorporated by reference in its entirety into this application.

The stent structures provided herein are exemplary only. Any framework that supports a patch against a vessel wall and permits the growth of a new tissue layer thereover is within the scope of the instant disclosure. Although an open stent structure is generally shown and described, in which one or more openings are positioned in the stent wall, other configurations may also be used. The openings may be of different sizes, such as those present in a woven configuration or in a mesh, fiber, or other stent or graft structure. Any such configuration is included in the term support scaffold. In an exemplary embodiment, the support scaffold is configured to approximately the interior vessel profile. For example, the support scaffold may be generally cylindrical or tubular in shape. The support scaffold may include apertures through the scaffold wall. The support scaffold may include connected struts that are expandable from a contracted configuration having a reduced diameter profile to an expanded configuration having an increased diameter profile larger than the reduced diameter profile. The support scaffold may also be made of different materials. For example, the stent may comprise stainless steel (e.g., AISI 316 SS), titanium, cobalt-chromium alloys, nickel titanium (Nitinol), Cobalt-Nickel alloy, metal, metal alloy, and combinations thereof. The stent may also be made of a bioresorbable materials, such as, for example, magnesium, zink, poly(L-lactide).

FIGS. 8A-8C illustrate an exemplary embodiment of a device 80 to produce a neovalve through a percutaneous minimally-invasive method. FIG. 8A illustrates a perspective view of the exemplary device while FIG. 8B illustrates a first side profile view and FIG. 8C illustrates a second side profile view orthogonal to the FIG. 8B side view. Exemplary embodiments include a stent or stent-like scaffold 86 and a patch 88 removeably attached to the scaffold. The device may include a retrieval component to remove the patch from the scaffold. The stent may comprise any pattern shown and described herein or known in the art, such as a self-expanding stent or a balloon expandable stent, and helical or circumferential configurations, without limitation. Exemplary stent configurations are provided above for illustration only and are not intended to limit the disclosure. A generic tubular structure is illustrated to represent the stent or stent-like scaffold without identifying any particular form to illustrate the interchangeability of the stent structures.

The device 80 includes a removeably attached patch 88 on a luminal surface of the stent 86. As shown, the patch covers only a portion of the luminal surface of the stent 80. The covered portion may not fully circumscribe the stent, such that the patch may not form a complete ring or closed loop. The patch may include a first and second terminal end. The first terminal end may be positioned at, adjacent, or proximate a terminal end of the stent. The first terminal end may define an arc length L1 around a portion of the interior circumference of the luminal surface of the stent. The arc defined by the first terminal end may circumscribe approximately half of the stent perimeter. For example, the patch may extend around 30-60 percent of the interior circumference of the stent. When seen in profile, the patch may extend symmetrically down toward the middle of the stent profile. For example, the patch may extend from a top edge to approximately 45-60 percent, or 48-55 percent, and approximately 50 percent across the stent diameter when seen in profile. The patch longitudinal length may also be approximately equal to or just less than the longitudinal length of the stent. In an exemplary embodiment, the patch length is 80 to 100 percent of the stent length, or 90-98 percent of the stent length.

In an exemplary embodiment, the patch tapers from the first end to the second end, such that the arc length of the first end L1 is greater than an arc length of the second end L2, where the arc length is measured perpendicular to the device axis. The patch may define other shapes. In an exemplary embodiment, the patch does not taper but maintains a constant arc length along its length thereby defining a rectangular patch when see in profile. The exemplary illustrated patch is illustrated in a dashed line to indicate its position on the interior surface of the stent structure.

In an exemplary embodiment, the patch 88 comprises a flexible or semi-flexible material that conforms to the luminal surface of the stent 86. The material is flexible or semi-flexible to permit movement of the device during navigation through tortious vessels to a delivery site within the vasculature of a patient. The material is flexible in that it may be deformed. The material may be semi-flexible in that it can retain its shape when unsupported by the scaffold structure, but flexible to contort under application of an outside force to navigate the tortuous lumens to the deployment site. In an exemplary embodiment, the patch is non-rigid in that is have sufficiently flexibility to crimp to the stent structure and define a reduced profile delivery configuration and an expanded profile deployed configuration.

The patch 88 may be made in various configurations and materials. For example, a thin metal sheet may be used. In an exemplary embodiment, the patch and the stent are made of the same material, such as Nitinol, steel, titanium, Cobalt-Nickel alloy, or metal or metal alloy. The patch may also or alternatively comprise a fine wire mesh. To reduce tissue ingrowth through the patch, the patch may be coated with another material. For example, a urethane may be used to coat the mesh and prevent tissue penetration through the mesh apertures. The patch may also include non-metal combinations. For example, the patch may include an expanded polytetrafluoroethylene (ePTFE).

The patch 88 may be coated with drugs to inhibit cell proliferation along a portion of the patch. In an exemplary embodiment, the patch 88 may be coated on an interior or luminal surface along a portion at and/or adjacent the terminal end of the patch. In this exemplary embodiment, the leading edge of the patch is not covered with a growth layer after implantation of the device because of the presence of the drug coating. Therefore, the patch may be more easily removed to create the neovalve. An exemplary coated region 89 is illustrated by a cross-hatch pattern in FIGS. 8B and 8C. The patch 88 may also be coated with a drug or include a surface texture to encourage cellular proliferation across a majority of the patch.

In an exemplary embodiment, the patch is removably coupled to the stent. The patch may be coupled to the stent in any fashion. For example, methods employed to couple grafts to stent surfaces may be used. The patch may be removably coupled to the stent by manipulating the bonding strength between the stent and the patch. For example, the patch may be adhered to the stent with sufficient strength to retain the patch in place despite the shear stress imposed by the blood passage. However, the adhesive strength may be overcome by the addition of an externally applied force, such as that imposed through a retrieval device, described in more detail herein. The attachment strength may also degrade over time, such as by use of resorbable or degradable agents. Therefore, when initially implanted, the patch may be more securely coupled to the stent when the experienced sheer stress is greatest. As the growth layer forms over the graft, the attachment strength between the stent and patch may be reduced as the growth layer may be used to provide the requisite support for the patch to retain it in place until it is removed.

In the case of a metallic patch or a patch including a metal component, the patch may be welded to the stent. The patch may be sufficiently thin to permit its removal by tearing or otherwise separating from the weld locations. In an exemplary embodiment, the patch is perforated or altered, such as by having a reduced thickness, to facilitate separation of the patch from the stent when an external force is applied. If the patch include a wire mesh, the mesh wire may be used to attach the patch to the stent.

In one embodiment, the stent 86 may include a coating. The coating may cover substantially the entire surface area of the stent structure corresponding to the patch area or may only cover a portion thereof. The coating may include a polymer that is capable of adhering to the patch 88, through the application of, for example, heat, pressure, solvents, adhesives (e.g., bio-resorbable adhesives), or combinations thereof. Suitable polymers for the coating may include, for example, polytetrafluoroethylene (PTFE), ePTFE, polyurethane, fluorinated ethylene propylene (FEP), an amorphous fluoropolymer, and combinations thereof. In a preferred embodiment, the polymer includes an amorphous fluoropolymer including tetrafluoroethylene (TEF) and 4,5-difluoro-2,2-bis(trifluoromethyl)-1,3-dioxole, or a perfluoroelastomer, as described in U.S. Pat. No. 7,476,246, which is incorporated by reference in its entirety into this application. The coating may be in the form of particles or powder, and may be applied to the stent 86 and/or to the patch 88 by spraying, dip coating, or other methods known to one skilled in the art. In one embodiment, the coating is a fluoropolymer including TEF in powdered form which is disposed directly on a surface of the patch 88 so that when the stent 86 is positioned on the surface, the powder is positioned between the patch and a surface of the stent.

Attachment of the stent to the patch may be accomplished by various methods, which can be facilitated by the materials chosen for the stent, patch and/or coatings, if used. For example, if an ePTFE patch is used, it may be positioned over a mandrel. The ePTFE patch may be sintered, unsintered, or partially sintered. A stent with a polyurethane coating may be positioned along the outer (abluminal) surface of the ePTFE patch. In one embodiment, the stent may be pre-dilated (expanded) by a tool for moving into position on an outer surface of the patch. Depending on the material properties of the stent, an additional crimping step may be required to secure the stent in position. Once the stent is initially positioned on a surface of the patch, the mandrel may then be removed from the assembly and the inside surface of the ePTFE patch may be sprayed, with a solvent, such as tetrahydrofuran (THF), so that the THF migrates through the wall of the patch. The spraying may be accomplished using different methods known to one skilled in the art. For example, the patch may be suspended such that a surface of the graft is accessible; a spraying mechanism may be inserted into the stent lumen and rotated to contact THF with a surface of the patch. Alternatively, a mandrel with openings may be inserted into the lumen, the mandrel attached to a source of THF, where the THF is delivered to the mandrel and through the openings to contact a surface of the patch. Another possibility includes using a needle device attached to a source of THF and inserting the needle through the wall of the stent at various locations, where THF is delivered through the needle at each location to contact a surface of the patch. The interaction between the ePTFE, THF and polyurethane coating on the stent bonds the annular members to the ePTFE graft (the THF or other aprotic solvent is believed to dissolve polyurethane, such that when a small amount contacts the polyurethane coating, a mechanical bond is developed between the coating and the ePTFE patch).

In another embodiment, a suitable solvent, such as, for example, an aprotic solvent including dimethylacetamide (DMAC), dimethylforamide, THF, or their mixtures, is sprayed or otherwise disposed over the outside surface of the patch after the stent has been positioned thereover. Alternatively, the ePTFE patch with the stent could be dip coated in a suitable solvent. In yet another embodiment, the stent is coated with PTFE and the ePTFE patch is initially unsintered. Following placement of the stent over the patch, the assembly is heated above the crystalline melt point of PTFE to sinter the stent to the patch.

It is within the scope of the present disclosure to provide a graft layer to facilitate attachment of the patch to the stent. For example, an annular graft member could be disposed on an outer surface of the stent and the patch attached to the stent and/or the graft member through openings in the stent wall. Therefore, the stent could be disposed between a generally tubular graft layer and strips of covering material defining a patch. The graft and/or patch may be perforated or otherwise altered at or proximate the attachment points to facilitate removal of the patch.

In one attachment method, stent 86, which may or may not include a coating, is woven into a portion of the patch. In one embodiment, annular members of a stent having a zig-zag configuration of struts are woven into the patch. In an exemplary embodiment, sutures may be used to attach the stent to the patch. The sutures may be resorbable, non-resorbable, or a combination of a set of sutures that are resorbable and a set of sutures that are not resorbable. In certain embodiments, additional or alternative attachment methods are used such as bonding, welding, weaving, sutures, spraying with a solvent, such as THF (e.g., the stent including a coating, such as polyurethane), disposing an adhesive, such as a bio-resorbable and/or non-bio-resorbable adhesive, over one or more surfaces of the patch (e.g., at locations of contact with the stent), heating the stent-patch (e.g., the ePTFE is unsintered and the stent includes a coating, such as PTFE), applying a uniform pressure to the assembled stent-patch along both inner and outer surfaces, or any combination thereof.

In an exemplary embodiment, the stent, the patch, the attachment mechanism between the patch and the stent, and any combination thereof may be resorbable such that the neovalve is created without the removal of the patch. In an exemplary embodiment, the attachment between the stent and the patch is resorbable such that after the growth of the growth layer, the patch and the growth layer together separate as a single layer from the stent and the vessel wall. In an exemplary embodiment, the patch is resorbable such that when the patch degrades, the growth layer separates from the stent and vessel wall. The attachment mechanism, such as the suture, adhesive, etc. and/or the patch may be resorbable by the application of a solvent or may be bioresorbable such that it degrades in the presence of blood or bodily fluid.

In an exemplary embodiment, the device may include multiple patches supported by a single stent. For example, two or more patches may be on opposing lateral sides of the stent such that once implanted and removed, the separated growth layers may form a valve similar to a duckbill valve. In an exemplary embodiment, two or more patches are circumferentially offset around a circumference of the stent and may be coextensive along a longitudinal length of the stent, such that the patches overlap when viewed in profile. The device may also include multiple patches longitudinally separated along a longitudinal length of the stent, such that a series of sequential valves would be created along a vein length. In this case, when seen in profile, the patch may extend symmetrically down toward the middle of the stent profile. For example, the patch may extend from a top edge to approximately 25-75 percent, or approximately 25-50 percent across the stent diameter when seen in profile and/or a second patch may extend from a bottom edge to approximately 25-75 percent, approximately 25-50 percent, or approximately 25 percent across the stent diameter when seen in profile. In an exemplary embodiment, three or four patches are used circumferentially offset around an interior perimeter of the stent.

Figure 9:
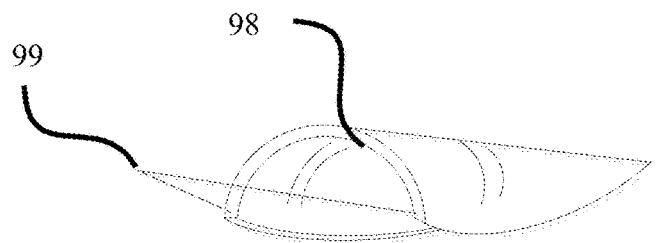
FIG. 9 illustrates an exemplary patch used in conjunction with embodiments described herein.

In an exemplary embodiment, the patch may also include a retrieval device. FIG. 9 illustrates an exemplary patch 98 comprising a retrieval device 99. The retrieval device may be any extension or feature that can be captured, snared, attached, grasped, or otherwise manipulated to provide a surface or structure to remove the patch after the growth layer has formed. As shown, the retrieval device provides a loop or hook that may be used in conjunction with a snare to permit an external force to pull and remove the patch from between the vessel wall/stent structure and the grown growth layer. The retrieval device may be positioned locally to the patch or may extend from the patch to a position outside of the body while the device is implanted. In an exemplary embodiment, the retrieval device is a loop permanently attached to the patch with a string or extension that is configured, when the device is implanted, to extend to a position outside of the body. The retrieval device is configured to transfer removal forces from a practitioner or snare to the patch and separate the patch from the stent and the grown growth layer. As shown, the retrieval device is permanently attached on opposite sides of the terminal end of the patch. However, any configuration of retrieval device may be used. In the case of a metal patch, the retrieval device may be welded to the patch. In the case of a wire mesh, the wires of the mesh may be extended to integrally form the retrieval device.

In an exemplary embodiment, the retrieval device is configured to be positioned in the center of the vessel when the patch is completely covered by the growth layer. In an exemplary embodiment, the retrieval device is configured to extend from the implant location to a position outside of the body. For example, a wire may be used that is permanently attached to the patch and is sufficiently long to extend from an intended implant site in a vein to a position outside of the body. The retrieval device may then act as a guidewire, permitting a retrieval sheath to be inserted thereover. When application of force is imposed on the patch through the retrieval device, it may be used to position the patch within a sheath positioned over the retrieval device, and both removed from the body.

Figure 10:
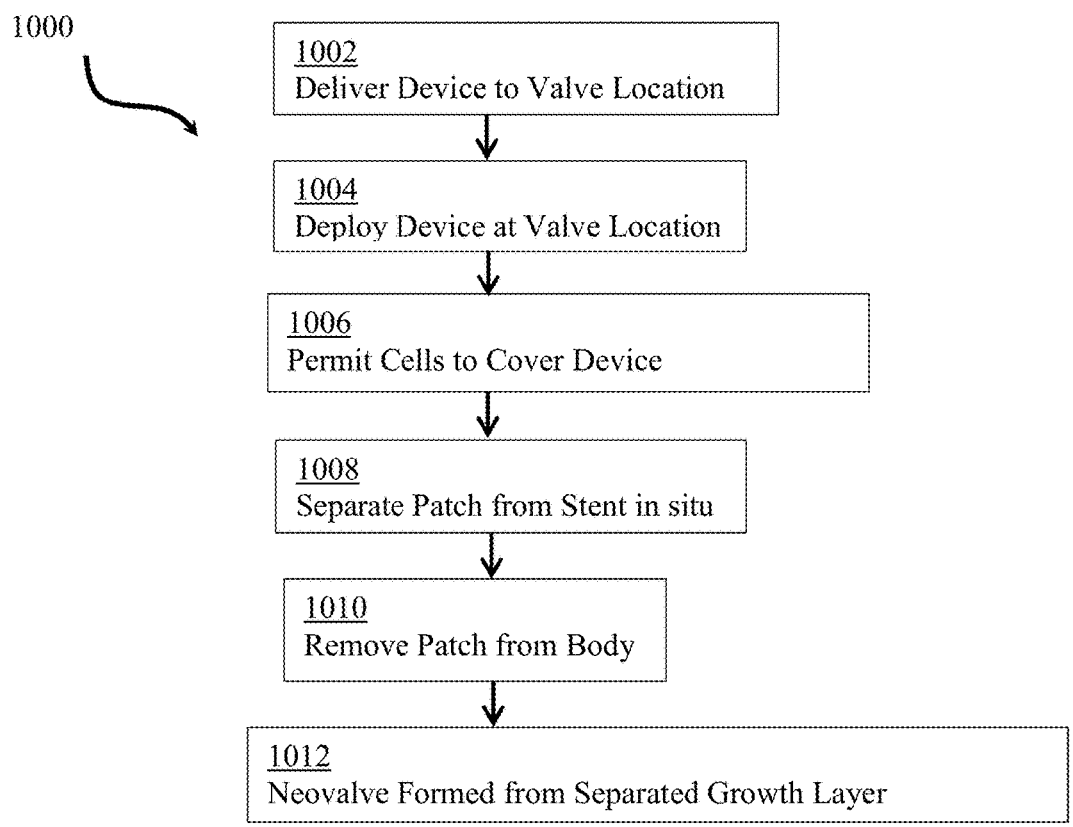
FIG. 10 represents an exemplary flow diagram to perform a method of creating a neovalve using embodiments described herein.

FIG. 10 illustrates an exemplary flow diagram 1000 of a method of using the device described herein to form a valve within the vein through minimally-invasive or less invasive procedures. As the foregoing text and figures may apparent, a method of creating the neovalve may include delivering a device comprising a stent scaffold and a patch on a luminal surface thereof to the target vein and leaving the device in place according to known stenting or similar methods. After a sufficient period of time, such that the device is covered by vascular smooth muscle cells, endothelial tissue, vascular tissue, and/or other cellular layer, the patch may be separated from the stent scaffold and removed from the body. The removal of the patch creates a slit in the vessel wall between the vein wall and the growth layer formed over the patch. The space left behind the patch within the vessel wall may be used to cause the vessel wall layers to separate and permit the luminal side of the wall to act as a valve similar to the surgical neovalve.

At step 1002, a device according to embodiments described herein may be delivered to a site within the body in which a valve is to be created. The device may define a reduced diameter delivery configuration positioned on the end of a delivery device. The delivery device may be a catheter that may include an outer sheath and/or inner catheter having a region to support the device and/or distal balloon. Navigating the device to a valve location and deploying the device at step 1004 may be similar to conventional methods for positioning and deploying a stent within the vasculature. The device, the delivery device, and combinations thereof may include visual markers or other system may be used to confirm the final location of the device before, during, and/or after deployment. Once deployed, at step 1006, the device is left in the body for a sufficient period of time to permit a layer of growth cells to completely or substantially cover the patch and/or stent. For example, the device may be implanted in the body for approximately 4 to 8 weeks. This step may also include preventing a portion of the patch from supporting cellular growth. For example, a drug to inhibit cellular or neointimal/endothelial proliferation may be coated or impregnated into or on a portion of the patch material, such that a portion of the patch, such as a leading edge of the patch is not covered by a cellular layer. At step 1008, once the growth layer is formed over the patch, the patch is separated from the stent and at step 1010, the patch is removed from the body. The patch may be separated through degradation of the attachment between the patch and the stent, and/or through application of an external force, device, reaction, or initiator. In an exemplary embodiment, a retrieval device is used to separate the patch and remove it from the body. The retrieval device may be permanently affixed to the patch and either directly or indirectly used to apply an external force or sheer force to the patch relative to the stent. In an exemplary embodiment, the retrieval device is configured such that it remains exposed in an interior of the vessel after the patch has been completely covered with the growth layer. At step 2012, the removal of the patch creates a gap between the growth layer and the stent and/or vessel wall. A valve is naturally formed by collapsing this separated tissue into the lumen of the vessel.

Figure 11A:
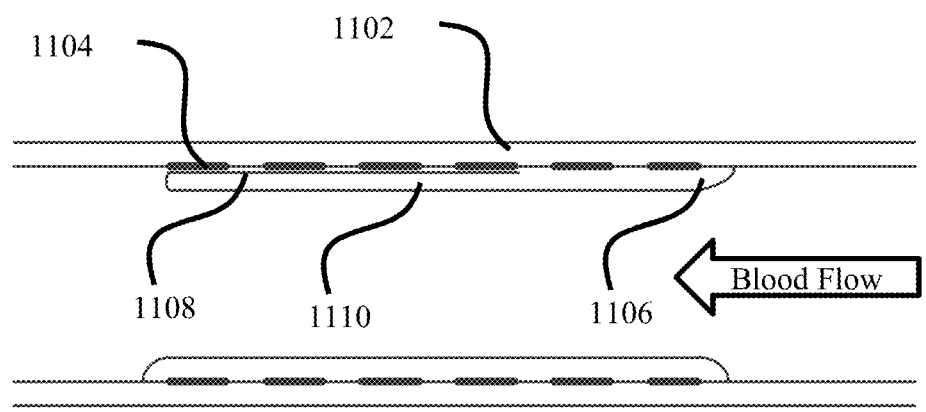
FIGS. 11A-11B illustrate the device as implanted in the body according to exemplary embodiments described herein.
Figure 11B:
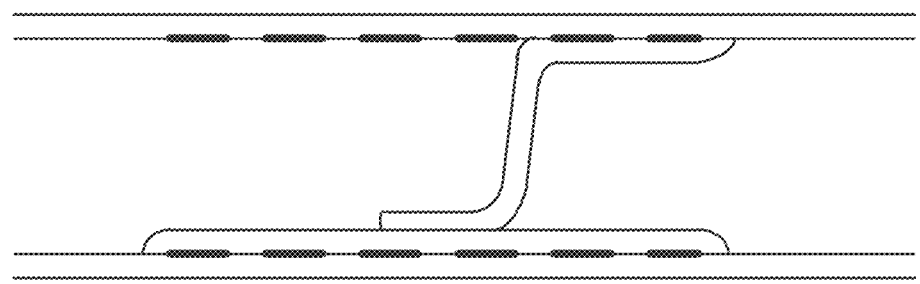

FIGS. 11A-11B illustrate an exemplary implantation of the device according to embodiments described herein after the patch has been removed. As shown, the device is positioned in a vessel 1102. After the patch has been removed, the device consists of the stent structure 1104. The device has been overgrown with an growth layer 1106. With the removal of the patch, a gap 1108 is left to form a flap or valve 1110. When the blood pressure moves the blood past the valve, as in FIG. 11A, the growth layer 1106 is pushed against the original or natural vessel wall 1102 and/or the stent 1104. When a back pressure is felt or a condition in which the blood would flow in an undesirable direction, illustrated in FIG. 11B, the flap or valve 1110 is pulled from the vessel wall 1102 and blocks the vessel lumen, thus preventing any back flow of blood. In an exemplary embodiment, the patch creates a slit at the forward edge and a pocket between the growth layer and the vessel wall. In this case, when the valve is closed, a surface approximating a portion of a cone or dome blocks the vessel lumen.

Although embodiments of this invention have been fully described with reference to the accompanying drawings, it is to be noted that various changes and modifications will become apparent to those skilled in the art. Such changes and modifications are to be understood as being included within the scope of embodiments of this invention as defined by the appended claims. For example, exemplary embodiments are provided with different combinations of features. However, any combination of components or features may be used and are within the scope of the instant disclosure. For example, components may be integrated, subdivided, duplicated, removed, added, or otherwise recombined and remain within the scope of the instant invention. Similarly, with respect to the exemplary methods, steps may be performed in various order, or steps may be recombined by duplicating, separating, integrating, removing or otherwise reconfiguring the steps and remain within the scope of the instant disclosure. It should also be understood that the term "comprising" is synonymous with "including" and does not mean "consisting only of". Any use of the terms "and" or "or" is intended to include the other, such that any list of options, features, or components may include any combination of the identified options unless expressly limited.

Also, any patent, patent application, or other cited reference is hereby incorporated by reference in its entirety. Any such cited reference or general description of the state of the art, background, or conventional system or method is not an admission that any such disclosure is prior art or forms part of the common general knowledge.

The invention claimed is:

1. An intraluminal device having an implanted configuration and a modified configuration following the implanted configuration, the intraluminal device comprising:

a support scaffold designed for implanting into a blood vessel, the support scaffold including a lumen defined by a luminal surface; and a patch coupled to the support scaffold along a length of the luminal surface in the implanted configuration, the patch covering less than a full circumference along the length, wherein removal of the patch from the lumen of the support scaffold transitions the intraluminal device from the implanted configuration to the modified configuration.

2. The intraluminal device of claim 1, wherein the patch includes a leading terminal edge positioned at a terminal end of the support scaffold, the leading terminal edge including a portion extending into the lumen of the support scaffold.

3. The intraluminal device of claim 1, wherein the patch defines a leading terminal edge and a trailing terminal edge, and wherein the leading terminal edge is configured to inhibit cellular proliferation in the implanted configuration.

4. The intraluminal device of claim 3, wherein the leading terminal edge comprises a coating including a drug to inhibit cellular proliferation.

5. The intraluminal device of claim 4, wherein the patch comprises a metal component welded to the support scaffold, and wherein the support scaffold has a thickness greater than a thickness of the metal component.

6. The intraluminal device of claim 1, wherein the support scaffold is a stent.

7. The intraluminal device of claim 6, further comprising a retrieval device permanently attached to the patch.

8. The intraluminal device of claim 7, wherein the retrieval device comprises a hook designed to be captured by a snare and pulled in order to remove the patch from the stent thereby transitioning the intraluminal device from the implanted configuration to the modified configuration.

9. The intraluminal device of claim 7, wherein the retrieval device comprises an extension positioned outside of the blood vessel in the implanted configuration, wherein the extension is designed to be manipulated in order to remove the patch from the stent thereby transitioning the intraluminal device from the implanted configuration to the modified configuration.

10. The intraluminal device of claim 3, wherein the patch tapers from the leading terminal edge to the trailing terminal edge such that an arc length defined by the patch at the leading terminal edge is longer than an arc length defined by the patch at the trailing terminal edge.

11. The intraluminal device of claim 1, wherein the support scaffold is a stent including a polyurethane coating, wherein the patch comprises ePTFE (expanded polytetrafluoroethylene), and wherein the ePTFE is bonded to the polyurethane coating.

12. An intraluminal device having an implanted configuration and a modified configuration following the implanted configuration, the intraluminal device comprising:

a stent including a lumen defined by a luminal surface, the stent comprising a metal material selected from the group consisting of Nitinol, steel, titanium, Cobalt-Nickel alloy, and a metal alloy; and a patch comprising the metal material, the patch covering a portion of the luminal surface of the stent in the implanted configuration, wherein removing the patch from the lumen of the stent transitions the intraluminal device from the implanted configuration to the modified configuration.

* * * * *